United States Patent

Sirrenberg et al.

Patent Number: 5,405,858
Date of Patent: Apr. 11, 1995

[54] FURAZANYLUREAS

[75] Inventors: Wilhelm Sirrenberg, Sprockhoevel; Reinhard Lantzsch, Wuppertal; Albrecht Marhold, Leverkusen; Ulrike Wachendorff-Neumann, Monheim; Alfred Elbert, Burscheid, all of Germany

[73] Assignee: Bayer Aktiengesellschaft, Leverkusen, Germany

[21] Appl. No.: 28,857

[22] Filed: Mar. 10, 1993

[30] Foreign Application Priority Data

Mar. 19, 1992 [DE] Germany .................. 42 08 873.9

[51] Int. Cl.$^6$ ............... C07D 271/08; A01N 47/36
[52] U.S. Cl. ................................. 514/364; 548/125
[58] Field of Search ................. 548/125; 514/364

[56] References Cited

U.S. PATENT DOCUMENTS

| | | | |
|---|---|---|---|
| 4,764,524 | 8/1988 | Sirrenberg et al. | 548/364 |
| 4,826,988 | 5/1989 | Sirrenberg et al. | 548/364 |
| 4,853,397 | 8/1989 | Sirrenberg et al. | 548/364 |
| 4,886,823 | 12/1989 | Sirrenberg et al. | 548/364 |
| 4,925,875 | 5/1990 | Drabek et al. | 548/364 |

FOREIGN PATENT DOCUMENTS

| | | |
|---|---|---|
| 1246587 | 12/1988 | Canada . |
| 0132680 | 2/1985 | European Pat. Off. . |
| 0156198 | 10/1985 | European Pat. Off. . |
| 0189043 | 7/1986 | European Pat. Off. . |
| 0253175 | 1/1988 | European Pat. Off. . |
| 0300968 | 1/1989 | European Pat. Off. . |
| 0316734 | 8/1989 | European Pat. Off. . |

*Primary Examiner*—Robert Gerstl
*Attorney, Agent, or Firm*—Sprung Horn Kramer & Woods

[57] ABSTRACT

The invention relates to the new furazanylureas of the general formula (I)

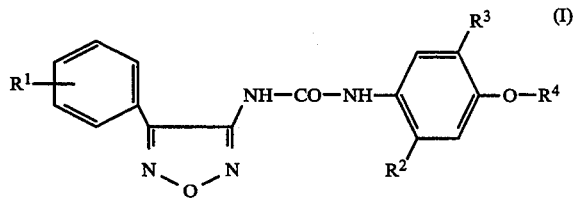

in which
R$^1$ represents hydrogen or fluorine,
R$^2$ represents hydrogen, fluorine or chlorine,
R$^3$ represents hydrogen, fluorine or chlorine and
R$^4$ represents phenyl which is substituted by trifluoromethyl and additionally monosubstituted to tetrasubstituted by fluorine and/or chlorine, and,
in the event that R$^1$ represents fluorine and/or R$^2$ and/or R$^3$ represent fluorine or chlorine, R$^4$ furthermore also represents difluoromethyl, trifluoromethyl, chlorodifluoromethyl, trifluoroethyl, tetrafluoroethyl, chlorotrifluoroethyl, hexafluoropropyl, hexafluoropropenyl or trifluoromethylphenyl, which can be used as pesticides.

9 Claims, No Drawings

FURAZANYLUREAS

The invention relates to new furazanylureas, to a process for their preparation, and to their use as pesticides, in particular as acaricides.

It has already been disclosed that certain furazanylureas such as, for example, 1-(4-(4-chloro-phenyl)-1,2,5-oxadiazol-3-yl)-3-(4-trifluoromethoxy-phenyl)-urea and 1-(5-(4-chloro-phenyl)1,2,5-oxadiazol-3-yl)-3-(2-chloro-4-(2,6-dichloro-4-trifluoromethyl-phenoxy)-phenyl)-urea, have acaricidal properties (cf. EP-A 0,132,680 or U.S. Pat. No. 4,699,916 as well as EP-A-0,316,734 or U.S. Pat. No. 4,886,823).

The new furazanylureas of the general formula (I)

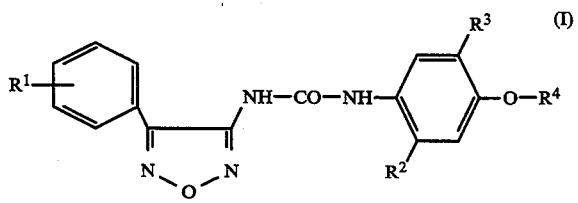

in which
$R^1$ represents hydrogen or fluorine,
$R^2$ represents hydrogen, fluorine or chlorine,
$R^3$ represents hydrogen, fluorine or chlorine and
$R^4$ represents phenyl which is substituted by trifluoromethyl and additionally monosubstituted to tetrasubstituted by fluorine and/or chlorine, and, in the event that $R^1$ represents fluorine and/or $R^2$ and/or $R^3$ represent fluorine or chlorine, $R^4$ furthermore also represents difluoromethyl, trifluoromethyl, chlorodifluoromethyl, trifluoroethyl, tetrafluoroethyl, chlorotrifluoroethyl, hexafluoropropyl, hexafluoropropenyl or trifluoromethylphenyl,
have now been found.

Furthermore, it has been found that the new furazanylureas of the general formula (I) are obtained when furazanyl isocyanates of the general formula (II)

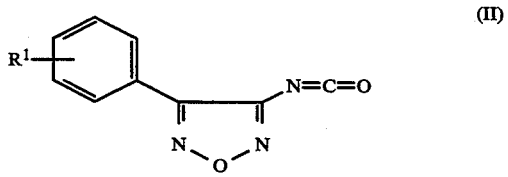

in which
$R^1$ has the abovementioned meaning
are reacted with amino compounds of the general formula (III)

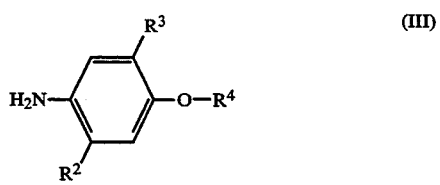

in which
$R^2$, $R^3$ and $R^4$ have the abovementioned meaning, if appropriate in the presence of a diluent.

The new compounds of the general formula (I) have properties which allow them to be used as pesticides; they have a good insecticidal action and are distinguished, in particular, by a very powerful acaricidal activity.

In the general formulae, fluorine $R^1$ is preferably in the 2- or 4-position, particularly preferably in the 2-position, of the phenyl ring.

$R^2$ in the general formulae preferably represents hydrogen or chlorine.

$R^3$ in the general formulae preferably represents hydrogen or chlorine.

In the phenyl ring $R^4$ which is substituted by trifluoromethyl, this group is in the 2-, 3- or 4-position, preferably in the 4-position. The phenyl ring which is additionally substituted by fluorine and/or chlorine contains 1 to 4, preferably 1, 2 or 3, fluorine and/or chlorine atoms, preferably chlorine atoms. Particularly preferred in this context are phenyl rings which are substituted by chlorine in the 2-position or in the 2-, 6-positions or in the 2-, 3-, 6-positions.

Chlorotrifluoroethyl $R^4$ preferably denotes —CF$_2$—CHFCl and hexafluoropropenyl preferably denotes —C(CF$_3$)=CHCF$_3$.

In the preferred compounds according to the invention (or the corresponding starting compounds), $R^1$ denotes hydrogen or 2-fluoro, $R^2$ denotes hydrogen or chlorine, $R^3$ denotes hydrogen and $R^4$ denotes 4-trifluoromethyl (where $R^1$ represents 2-fluoro), 4-trifluoromethyl-2,6-dichlorophenyl or 4-trifluoromethyl-2,3,6-trichlorophenyl.

Preferred new furazanylureas of the formula (I) are those in which
$R^1$ represents hydrogen or fluorine,
$R^2$ represents hydrogen, fluorine or chlorine,
$R^3$ represents hydrogen, fluorine or chlorine and
$R^4$ represents phenyl which is substituted in the para-position (4-position) by trifluoromethyl and additionally monosubstituted to trisubstituted by fluorine and/or chlorine, and,
in the event that $R^1$ represents fluorine and/or $R^2$ and/or $R^3$ represent fluorine or chlorine, $R^4$ additionally also represents difluoromethyl, trifluoromethyl, chlorodifluoromethyl, trifluoroethyl, tetrafluoroethyl, chlorotrifluoroethyl, hexafluoropropyl or hexafluoropropenyl.

The abovementioned preferred definitions apply in each case analogously to these combinations of radicals.

If, for example, 3-isocyanato-4-phenyl-1,2,5-oxadiazole and 3-fluoro-4-chlorodifluoromethoxy-aniline are used as starting substances, the course of the reaction in the process according to the invention can be represented by the following equation:

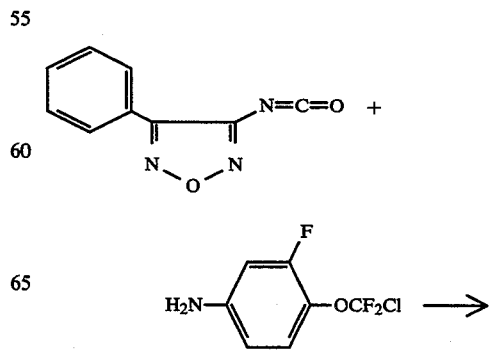

-continued

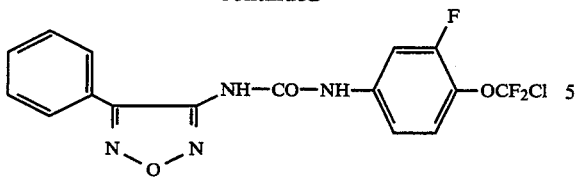

The furazanyl isocyanates of the formula (II) which are to be used as starting substances are known and/or can be prepared by processes known per se (cf. EP-A 0,132,680; U.S. Pat. No. 4,699,916; U.S. Pat. No. 4,826,988; EP-A 156,198).

The amino compounds of the formula (III) which are also to be used as starting substances are equally known and/or can be prepared by processes known per se (cf. DE-OS (German Published Specification) 2,411,320, EP-A 161,019, EP-A 216,423, DE-OS (German Published Specification) 3,603,089).

The amino compounds of the formula (III) in which
$R^2-$ represents fluorine or chlorine (preferably chlorine),
$R^3$ represents hydrogen, fluorine or chlorine and
$R^4$ represents phenyl which is substituted in the para-position (4-position) by trifluoromethyl and additionally disubstituted or trisubstituted (preferably in the 2,6-position or in the 2,3,6-position) by fluorine and/or chlorine (preferably by chlorine)
are new and form part of the present invention.

The new compounds of the formula (III) are obtained when aminophenols of the general formula (IV)

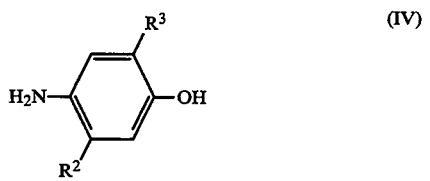

in which
$R^2$ and $R^3$ have the abovementioned meaning,
are reacted with halogen compounds of the general formula (V)

$$X-R^4 \quad (V)$$

in which
$R^4-$ has the abovementioned meaning and
X represents halogen, in particular fluorine or chlorine,
in the presence of an acid acceptor such as, for example, potassium carbonate, and in the presence of a diluent such as, for example, N-methyl-pyrrolidone, at temperatures of between 50° C. and 150° C., and the product is worked up by customary methods (cf. the Preparation Examples).

The process according to the invention for the preparation of the new furazanylureas of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

When carrying out the process according to the invention, the reaction temperatures can be varied within a substantial range. The process is preferably carried out at temperatures between 0° C. and 200° C., particularly preferably at temperatures between 20° C. and 150° C.

The process according to the invention is preferably carried out under atmospheric pressure. However, it is also possible to carry out the process under increased or reduced pressure.

To carry out the process according to the invention, the starting substances required in each case are preferably employed in approximately equimolar amounts. However, it is also possible to use one of the two components employed in each case in a larger excess. The reactions are preferably carried out in a suitable diluent, and the reaction mixture is stirred for several hours at the temperature required in each case. Working-up in the process according to the invention is carried out in each case by customary methods (cf. the Preparation Examples).

The active compounds are suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Phylloxera vastatrix, Pemphigus spp., Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata,*

*Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella Pieris spp., Chilo spp., Pyrausta nubilalis, Ephesti kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Atomaria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Cono derus spp., Melolontha melolontha, Amphimallon solsti tialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

From the order of the Arachnida, for example, *Scorpio maurus* and *Latrodectus mactans.*

From the order of the Acarina, for example, *Acarus siro, Argas spp., Ornithodorus spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp.*

The compounds of the formula (I) according to the invention are distinguished by a powerful insecticidal and, in particular, a powerful acaricidal activity, in particular against eggs (ovicidal action) and against the larvae (larvicidal action) of the pests.

In particular when employed as acaricides, they show an outstanding action on eggs and larvae of the greenhouse red spider mite (*Tetranychus urticae*) and the fruit tree red spider mite (*Panonychus ulmi*) and have a very good activity against virtually all development stages of spider mites.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, attractants, sterilising agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

Preferred pesticides according to the invention contain, in addition to the active compounds according to the invention and, if appropriate, besides customary auxiliaries and carriers, at least one surface-active substance (preferably a substance which acts as emulsifier and/or as wetting agent).

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

All percentages in the present text mean percent by weight unless specified otherwise.

The preparation of the compounds according to the invention will be illustrated with the aid of the following examples.

PREPARATION EXAMPLES

Example 1

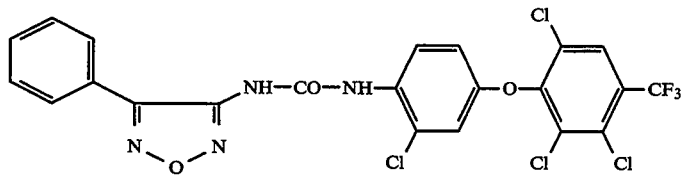

A solution of 1.5 g (8 mmol) of 3-isocyanato-4-phenyl-1,2,5-oxadiazole in 8 ml of toluene is added dropwise at 20° C. to a solution of 3.13 g (8 mmol) of 2-chloro-4-(2,3,6-trichloro-4-trifluoromethyl-phenoxy)-aniline in 50 ml of toluene, with stirring. The reaction mixture is then stirred for 60 minutes at 80° C. and again allowed to cool to 20° C. The product which has been obtained in crystalline form is isolated by filtration with suction.

3.1 g (65% of theory) of 1-[2-chloro-4-(2,3,6-trichloro-4-trifluoromethyl-phenoxy)-phenyl]-3-(4-phenyl-1,2,5-oxadiazol-3-yl)-urea of melting point 209° C. are obtained.

Other compounds of the formula (I) which can be prepared analogously to Example 1 and following the general description of the preparation process according to the invention are, for example, those listed in Table 1 below.

TABLE 1

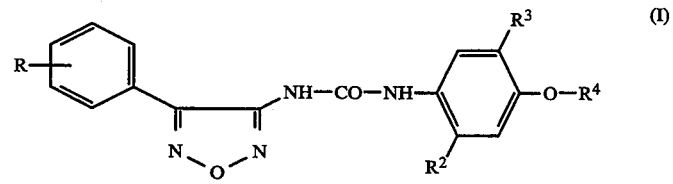

Examples of the compounds of the formula (I)

| Ex. No. | (Position) R$^1$ | R$^2$ | R$^3$ | R$^4$ | Melting point (°C.) |
|---|---|---|---|---|---|
| 2 | H | Cl | H | 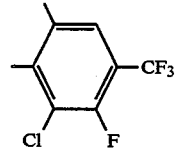 | 201 |
| 3 | (4-)F | H | H | 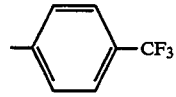 | |

TABLE 1-continued

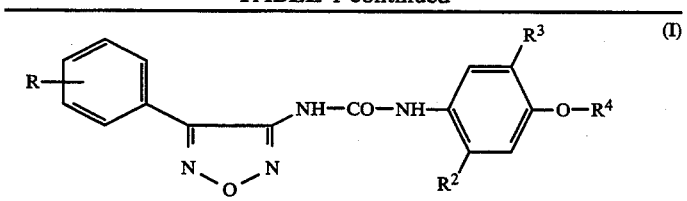

Examples of the compounds of the formula (I)

| Ex. No. | (Position) R¹ | R² | R³ | R⁴ | Melting point (°C.) |
|---|---|---|---|---|---|
| 4 | H | H | Cl | CF$_3$ | |
| 5 | H | H | Cl | —CF$_2$CHFCl | |
| 6 | H | H | Cl | —CF$_2$CHF$_2$ | |
| 7 | (4-)F | H | H | —CF$_2$CHFCl | |
| 8 | (4-)F | H | H | —CF$_2$CHF$_2$ | |
| 9 | H | H | Cl | —CF$_2$CHFCl | 214 |
| 10 | H | Cl | H | —CF$_2$CHFCl | 170 |
| 11 | (4-)F | H | Cl | —CF$_2$CHF$_2$ | 209 |
| 12 | (4-)F | H | Cl | —CF$_2$CHFCl | 202 |
| 13 | (4-)F | H | H | CF$_3$ | 193 |
| 14 | (4-)F | H | H | CHF$_2$ | 190 |
| 15 | (4-)F | H | H | 2-Cl-4-CF$_3$-phenyl | 209 |
| 16 | (4-)F | H | H | 2,5-di-Cl-4-CF$_3$-phenyl | 239 |
| 17 | H | Cl | H | 2,5-di-Cl-4-CF$_3$-phenyl | 211 |
| 18 | (4-)F | Cl | H | 2,5-di-Cl-4-CF$_3$-phenyl | 212 |
| 19 | (2-)F | H | H | —CF$_2$CHFCl | 216 |
| 20 | (2-)F | H | H | CF$_3$ | 204 |
| 21 | (2-)F | H | H | —CF$_2$CHF$_2$ | 206 |
| 22 | (2-)F | H | Cl | —CF$_2$CHFCl | 199 |
| 23 | H | F | H | —CF$_2$CHFCF$_3$ | 208 |
| 24 | (4-)F | F | H | —CF$_2$CHFCF$_3$ | 205 |
| 25 | (2-)F | H | Cl | CF$_3$ | 214 |
| 26 | (2-)F | H | H | CF$_2$Cl | 204 |
| 27 | (2-)F | H | H | —CF$_2$CHFCF$_3$ | 210 |
| 28 | (2-)F | F | H | —CF$_2$CHFCF$_3$ | |
| 29 | (2-)F | H | H | CHF$_2$ | 201 |
| 30 | (2-)F | Cl | H | —C(CF$_3$)=CHCF$_3$ | 196 |
| 31 | H | H | Cl | —CH$_2$CF$_3$ | 208 |
| 32 | (4-)F | H | H | —CH$_2$CF$_3$ | 210 |
| 33 | (2-)F | H | H | —CH$_2$CF$_3$ | 209 |
| 34 | (4-)F | H | Cl | —CH$_2$CF$_3$ | 196 |
| 35 | (2-)F | H | Cl | —CH$_2$CF$_3$ | 196 |
| 36 | H | F | H | CF$_3$ | |
| 37 | (4-)F | F | H | CF$_3$ | |

TABLE 1-continued

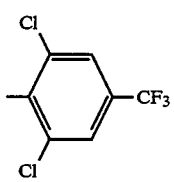

Examples of the compounds of the formula (I)

| Ex. No. | (Position) R$^1$ | R$^2$ | R$^3$ | R$^4$ | Melting point (°C.) |
|---|---|---|---|---|---|
| 38 | (2-)F | F | H | CF$_3$ | |
| 39 | H | F | H | CF$_2$Cl | |
| 40 | (4-)F | F | H | CF$_2$Cl | |
| 41 | (2-)F | F | H | CF$_2$Cl | |
| 42 | H | F | H | 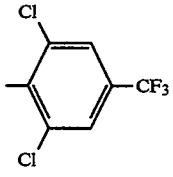 | |
| 43 | (4-)F | F | H | 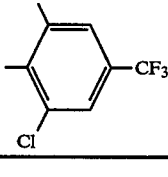 | |
| 44 | (2-)F | F | H | 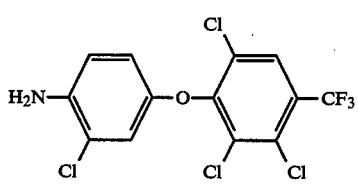 | |

STARTING SUBSTANCES OF THE FORMULA (III)

Example (III-1)

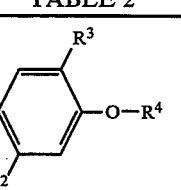

A mixture of 7.5 g (0.05 mol) of 3-chloro-4-aminophenol, 14.3 g (0.05 mol) of 2,3,4,5-tetrachloro-benzotrifluoride and 6.9 g (0.05 mol) of potassium carbonate in 35 ml of N-methyl-pyrrolidone is stirred for 4 hours at 125° C. to 130° C., and then, with stirring, poured into approximately twice the volume of water and filtered. The solid crude product is taken up in hot diisopropyl ether and the mixture is filtered. The filtrate is concentrated to approximately half its volume, and the product crystallises and is isolated by filtration with suction.

19 g (97% of theory) of 2-chloro-4-(2,3,6-trichloro-4-trifluoromethyl-phenoxy)-aniline of melting point 128° C. are obtained.

Other new compounds of the formula (III) which can be prepared analogously to Example (III-1) are, for example, those listed in Table 2 below.

TABLE 2

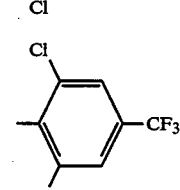

Examples of the compounds of the formula (IIIa)

| Ex. No. | R$^2$ | R$^3$ | R$^4$ | Physical data |
|---|---|---|---|---|
| IIIi-2 | Cl | H | (2,6-dichloro-4-CF$_3$-phenyl) | |
| III-3 | Cl | F | (2,6-dichloro-4-CF$_3$-phenyl) | |

TABLE 2-continued

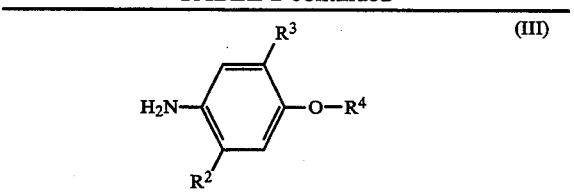

Examples of the compounds of the formula (IIIa)

| Ex. No. | R² | R³ | R⁴ | Physical data |
|---|---|---|---|---|
| III-4 | Cl | H | 4-CF₃-2-F-3,6-diCl-phenyl | |
| III-5 | Cl | F | 4-CF₃-2-F-3,6-diCl-phenyl | |
| III-6 | Cl | H | 4-CF₃-2-F-6-Cl-phenyl | |
| III-7 | Cl | H | 4-CF₃-2,3-diF-6-Cl-phenyl | |
| III-8 | Cl | F | 4-CF₃-2-F-6-Cl-phenyl | |
| III-9 | Cl | F | 4-CF₃-2,6-diF-3-Cl-phenyl | |
| III-10 | Cl | H | 4-CF₃-2,6-diF-phenyl | |
| III-11 | Cl | H | 4-CF₃-2,3-diF-phenyl | |

TABLE 2-continued

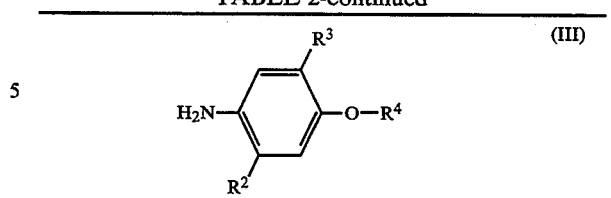

Examples of the compounds of the formula (IIIa)

| Ex. No. | R² | R³ | R⁴ | Physical data |
|---|---|---|---|---|
| III-12 | Cl | F | 4-CF₃-2,3-diF-phenyl | |
| III-13 | Cl | H | 4-CF₃-2,3-diCl-phenyl | |
| III-14 | Cl | F | 4-CF₃-2,3-diCl-phenyl | |

The biological activity of the compounds according to the invention will be illustrated with the aid of the following examples:

USE EXAMPLES

Example A

Tetranychus Test (OP-resistant)
Solvent: 7 parts by weight of dimethylformamide
Emulsifier: 1 part by weight of alkylaryl polyglycol ether To prepare a suitable preparation of active compounds, 1 part by weight of active compound is mixed with the stated amount of solvent and the stated amount of emulsifier, and the concentrate is diluted to the desired concentrations using emulsifier-containing water.

Bean plants (*Phaseolus vulgaris*) which are heavily populated with all development stages of the greenhouse red spider mite (*Tetranychus urticae*) are sprayed with a preparation of active compound of the desired concentration.

After the desired time, the action is determined in %. 100% denotes that all spider mites have been killed; 0% denotes that no spider mites have been killed.

In this test, a destruction rate of the spider mites of at least 90% after 14 days was shown, for example, by the compounds of Preparation Examples (2) and (17) at a concentration of 0.000032% and by the compound of Preparation Example (20) at a concentration of 0.00016%.

We claim:
1. A furazanylurea of the formula

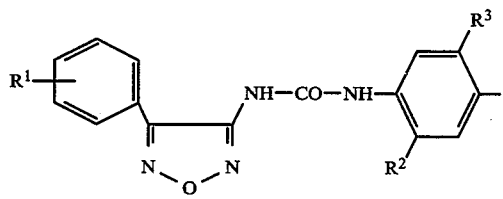

in which
- $R^1$ represents hydrogen,
- $R^2$ represents hydrogen, fluorine or chlorine,
- $R^3$ represents hydrogen, fluorine or chlorine and
- $R^4$ represents phenyl which is substituted by trifluoromethyl and additionally monosubstituted to tetrasubstituted by fluorine and/or chlorine, and,
  in the event that $R^2$ and/or $R^3$ represent fluorine or chlorine, $R^4$ furthermore also represents difluoromethyl, trifluoromethyl, chlorodifluoromethyl, trifluoroethyl, tetrafluoroethyl, chlorotrifluoroethyl, hexafluoropropyl, hexafluoropropenyl or trifluoromethylphenyl.

2. A furazanylurea according to claim 1, in which
- $R^1$ represents hydrogen,
- $R^2$ represents hydrogen, fluorine or chlorine,
- $R^3$ represents hydrogen, fluorine or chlorine and
- $R^4$ represents phenyl which is substituted in the para-position (4-position) by trifluoromethyl and additionally monosubstituted to trisubstituted by fluorine and/or chlorine, and,
  in the event that $R^2$ and/or $R^3$ represent fluorine or chlorine, $R^4$ additionally also represents difluoromethyl, trifluoromethyl, chlorodifluoromethyl, trifluoroethyl, tetrafluoroethyl, chlorotrifluoroethyl, hexafluoropropyl or hexafluoropropenyl.

3. A furazanylurea according to claim 1, of the formula

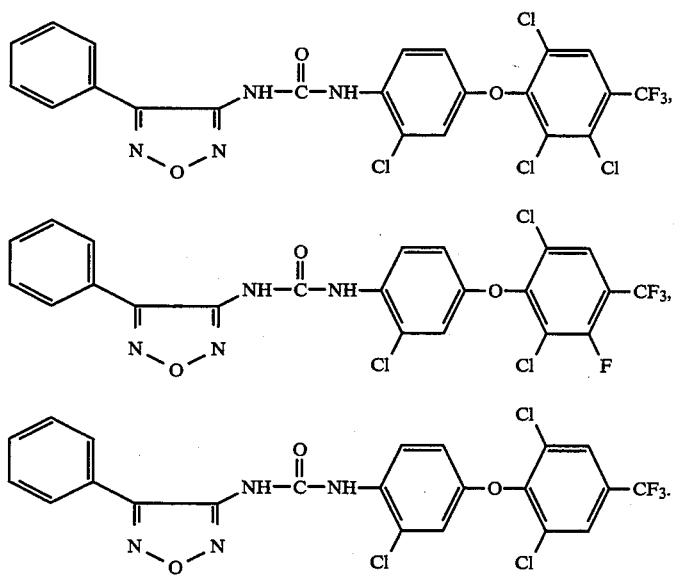

4. An acaricidal composition comprising a pesticidally effective amount of at least one furazanylurea according to claim 1 and a suitable extender or carrier.

5. A method of combating acarids comprising applying to said acarids or to a habitat thereof a pesticidally effective amount of a furazanylurea according to claim 1.

6. A method of combating insects comprising applying to said insects or a habitat thereof an insecticidally effective amount of furazanylurea according to claim 1.

7. A furazanylurea of the formula

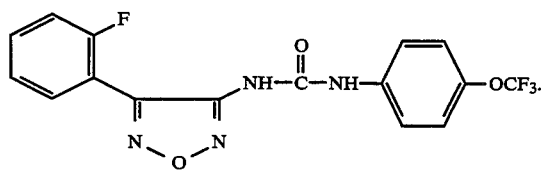

8. A method of combating pests comprising applying to said pests or to a habitat thereof a pesticidally effective amount of a furazanylurea according to claim 7.

9. A method of combating insects comprising applying to said insects or a habitat thereof an insecticidally effective amount of a furazanylurea according to claim 7.

* * * * *